United States Patent [19]

Lamont

[11] Patent Number: 5,453,082
[45] Date of Patent: Sep. 26, 1995

[54] PROTECTIVE MEDICAL BOOT WITH PNEUMATICALLY ADJUSTABLE ORTHOTIC SPLINT

[76] Inventor: William D. Lamont, 54283 Meadowood Ct., Shelby Township, Macomb County, Mich. 48316

[21] Appl. No.: 194,302

[22] Filed: Feb. 7, 1994

Related U.S. Application Data

[63] Continuation-in-part of Ser. No. 90,895, Jun. 12, 1993, Pat. No. 5,367,789, which is a continuation-in-part of Ser. No. 763,335, Sep. 20, 1991, Pat. No. 5,226,245.

[51] Int. Cl.$^6$ ...................................................... A61F 5/00
[52] U.S. Cl. .............................. 602/27; 602/13; 602/16; 128/882; 601/27; 601/148
[58] Field of Search ........................... 602/5, 13, 16, 602/23, 27, 28; 601/23, 27, 29, 31, 148, 97; 128/882, 845

[56] References Cited

U.S. PATENT DOCUMENTS

| | | |
|---|---|---|
| 4,003,374 | 1/1977 | Mizrachy . |
| 4,320,749 | 3/1982 | Highley ........................ 602/27 |
| 5,218,954 | 6/1993 | van Bennmelen .............. 602/13 X |
| 5,226,245 | 7/1993 | Lamont . |

*Primary Examiner*—Linda C. M. Dvorak
*Attorney, Agent, or Firm*—Charles W. Chandler

[57] ABSTRACT

A protective medical boot for treating or avoiding decubitus ulcers has an outer leg covering formed with a pair of cover panels having their seams hot-stamped together to provide a soft edge. An orthotic splint has a leg portion that is supported adjacent the back of the patient's leg, and a foot portion that supports the sole of the patient's foot. A heel device connects the leg portion to the foot portion at a selected angle with respect to the leg portion. A pneumatically-operated bladder is disposed between the foot portion and the patient's foot to provide a very fine adjustment of the angle of the patient's foot to his leg to assist in preventing or treating contracture of the patient's foot.

9 Claims, 3 Drawing Sheets

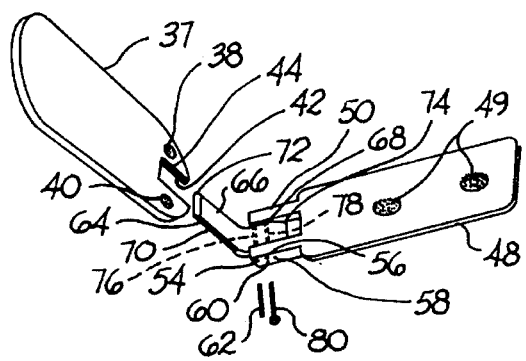
FIG. 6
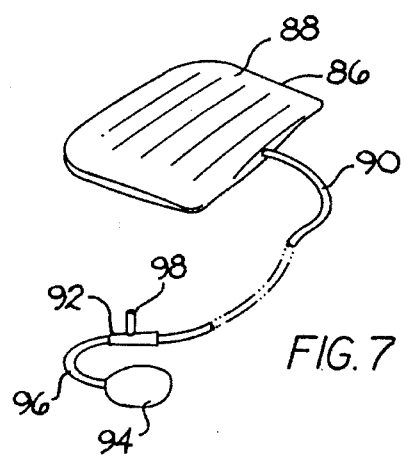
FIG. 7
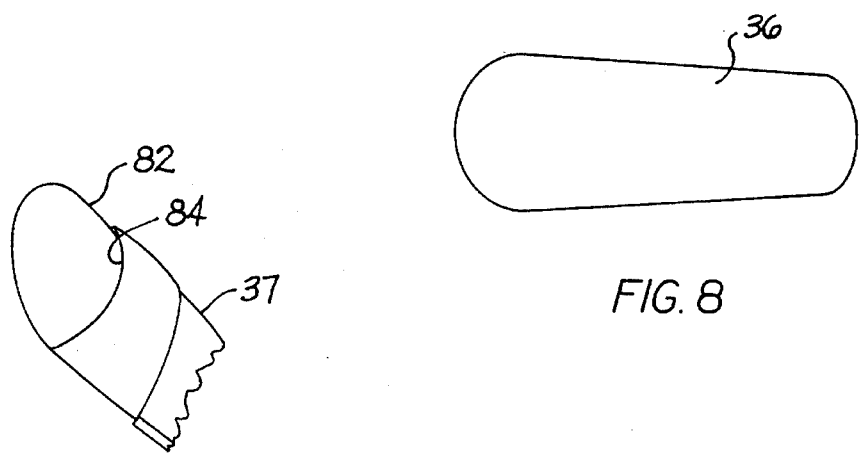
FIG. 8
FIG. 9

PROTECTIVE MEDICAL BOOT WITH PNEUMATICALLY ADJUSTABLE ORTHOTIC SPLINT

CROSS-REFERENCE TO RELATED APPLICATION

This application is a continuation-in-part of my patent application Ser. No. 90,895 filed Jul. 12, 1993 for "Protective Medical Boot and Orthotic Splint" which has since issued as U.S. Pat. No. 5,367,789 on Nov. 29, 1984, which in turn was a continuation-in-part of U.S. Pat. No. 5,226,245 issued Jul. 13, 1993 from application Ser. No. 763,335 filed Sep. 20, 1991.

BACKGROUND OF THE INVENTION

This invention is related to a medical boot for avoiding ulcers, and a supporting splint for treating a contracture condition of the patient's foot.

My co-pending application, and my prior U.S. Pat. No. 5,226,245 which was issued Jul. 13, 1993 for "Protective Boot Structure" disclose a soft medical boot for covering a patient's foot to prevent decubitus ulcers. The boot has panels formed of a soft material which are stitched around their edges. Occasionally the stitched edges tend to abrade the patient's skin.

In my co-pending patent application, I disclosed an orthotic splint having a leg portion and a foot portion. A heel device allows the user to quickly and easily set the splint at three positive positions. The three positions are 0° for holding the foot at a normal upright position when the user's leg is in a horizontal position; −30° for plantar flexion; and +10° for dorsi flexion.

Patients with a contracture condition, that is the foot tends to droop downward from the normal upright position, require a periodic adjustment of the position of the foot to stretch the leg muscles. The orthotic splint of my co-pending application provides adjustments in fairly large increments. The increments are determined by the location of the locking pin holes in the heel locking device. Patients having a contracture condition can be better assisted by having their foot position adjusted in smaller increments.

SUMMARY OF THE INVENTION

The broad purpose of the present invention is to provide an improved medical boot for preventing decubitus ulcers by hot-stamping the boot seams to provide a very soft seam that avoids abrading either the foot wearing the boot or the companion uncovered foot and ankle.

The present invention includes an inflatable bladder mounted between the hard sole of the orthotic splint and the sole of the patients foot. The treating nurse can adjust the plantar position of the user's foot in very small increments by inflating or deflating the bladder. Adjustments can be made periodically, that is, every few hours by simply squeezing an inflatable bulb to increase the volume of the bladder, or manipulating a valve to bleed air from the bladder to reduce its volume.

A flatter bladder can be employed under the patient's ankle to adjust the height of his heel in the boot to avoid heel ulcers. The bladder permits very small adjustments in height of the patient's heel to accommodate anatomical variations in different patients.

Still further objects and advantages of the invention will become readily apparent to those skilled in the art to which the invention pertains upon reference to the following detailed description.

DESCRIPTION OF THE DRAWINGS

The description refers to the accompanying drawings in which like reference characters refer to like parts throughout the several views, and in which:

FIG. 6 is a view of the splint;

FIG. 7 is a view of the bladder;

FIG. 8 is a view of the moveable sole located between the patient's foot and the bladder; and FIG. 9 illustrates a fabric pocket for supporting the bladder.

DESCRIPTION OF THE PREFERRED EMBODIMENT

Figure 1:
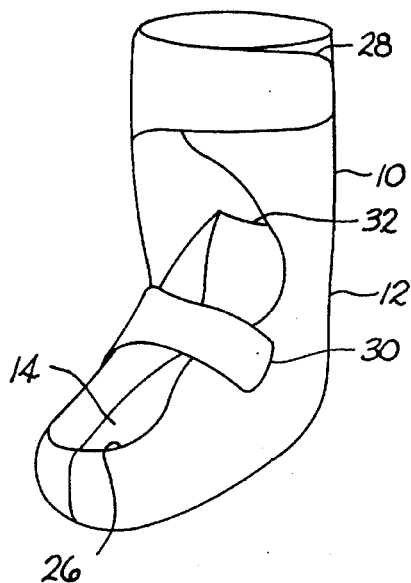
FIG. 1 is a view of a protective medical boot illustrating the preferred embodiment of the invention.
Figure 2:
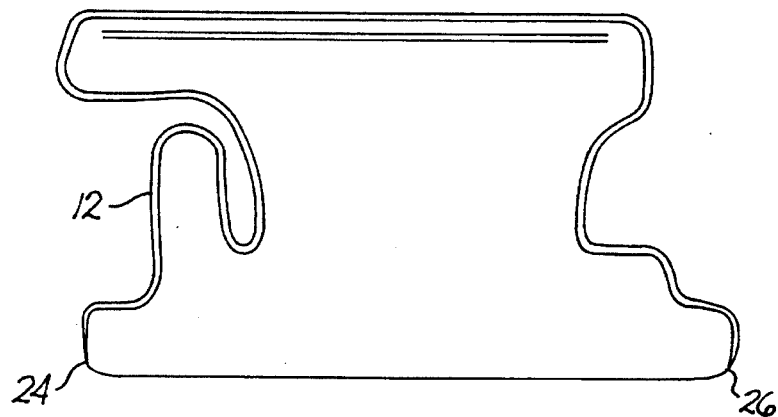
FIG. 2 is a view of the ankle portion of the boot prior to being joined to the sole, to illustrate the location of the hot stamped edges.
Figure 3:
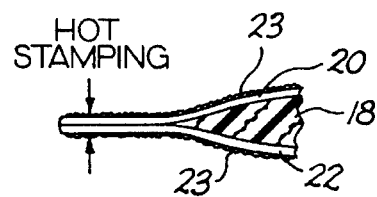
FIG. 3 is an enlarged cross-sectional view of a typical hot stamped, stitchless edge.

Referring to FIGS. 1–3, a preferred medical boot 10 comprises an upper portion 12 and a bottom sole 14. A general configuration of the boot is described in my co-pending application. The upper portion 12 is illustrated in FIG. 2 to show the profile of the boot edges before being assembled with the boot sole.

Referring to FIG. 3, both the upper portion of the boot and the sole are formed of an elastomeric shape-retaining material such as a soft, flexible, compressible, open-core polyurethane foam core 18, inner cover 20 and outer cover 22 of an ultra smooth, soft, non-allergenic cloth such as brushed tricot. This type of cloth is characterized by a continuous layer of small loops 23 which make the material compatible (engageable) with fabric hook fastener means such as Velcro fabric fasteners. The entire inner and outer covers of both the upper portion of the boot and the sole have a brushed tricot covering so that a patch of a Velcro-type hook material can be releasably connected in any location on the boot.

Referring to FIG. 2, the seam of the upper portion of the boot, beginning at a point 24 and extending generally in a clockwise direction around the profile of the boot to point 26, of the two layers 20 and 32 are joined together in a continuous attachment by a hot-stamping process. The seam thus is a stitchless type of connection which is relatively soft and avoids abrading any sensitive skin of the patient.

In all other substantial respects, the boot construction is identical to the soft boot illustrated in my co-pending patent application.

The front of the boot defines an opening 26, as illustrated in FIG. 1. A leg strap 28 provides means for fastening the boot to the patient's leg by means of fabric fasteners (not shown). The boot also has an ankle strap 30 for connecting the boot to the patient's ankle by means of fabric fastener means.

Figure 5:
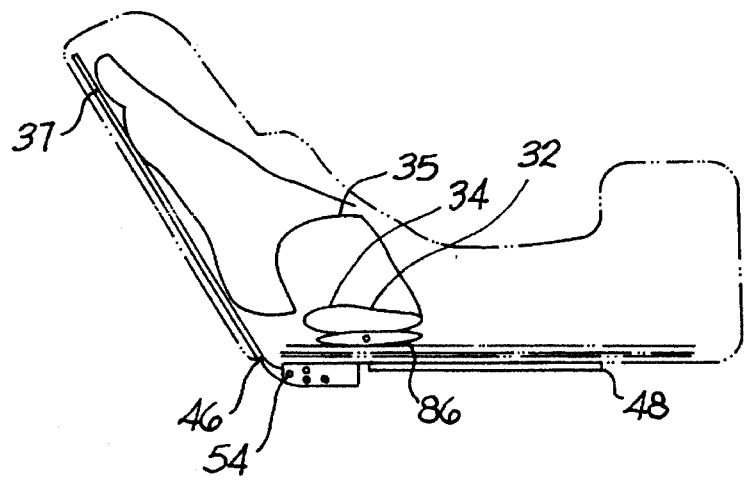
FIG. 5 is a view similar to FIG. 4 but showing the bladder located beneath the user's ankle to adjust the height of the heel.

The boot has an internal cushion 32, illustrated in FIGS. 1 and 5, which is identical to the cushion illustrated in my copending application. The cushion has a central portion 34 and a wing 35 (only one shown). The cushion is similar in construction to the boot, that is, formed with an inner core of a flexible, compressible, open core, polyurethane foam with an outside covering of a brushed tricot material, that is, a material having a continuous surface of closed loops. The cushion is attached to the internal boot cover by a fabric fastener (not shown). The central body portion and the two wings of the cushion each have an internally mounted flexible plastic sac (not shown) of a fluid which contains an internal/air/water/gel material and which is more fully disclosed in my co-pending patent application.

Figure 4:
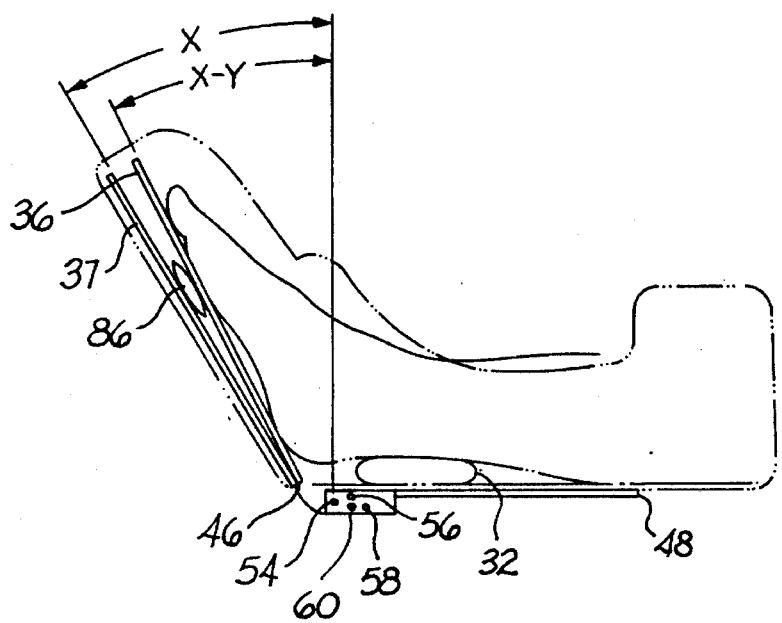
FIG. 4 is a view of the user's foot superimposed over the outline of a boot to show the foot and the orthotic splint in a position of plantar flexion.

Referring to FIGS. 4, 5, and 8, insole 36 is used in the boot. Insole 36 is soft and has an edge configuration slightly smaller than the sole of the boot to protect the bottom of the user's foot. Insole 36 is made with the same construction as the boot that is with a compressible inner liner, a brush tricot covering and a hot-stamped continuous edge around its periphery.

Hard sole 37 is also located in the boot adjacent the boots sole. Sole 37 is formed of a relatively rigid polypropylene plastic material with an outside contour slightly smaller than the soft insole and a ¼" thickness. Sole 37 is inserted in the bottom of the boot and connected to the bottom of the soft insole by two patches of hook fabric fasteners 38 and 40 which are attached to one side of the hard insole adjacent the heel, as best shown in FIG. 6. Patches 38 and 40 are attached to the brushed tricot covering of the soft insole.

Referring to FIG. 6, the heel end of the hard insole has a slot 42 which is 1" wide and ⅜" deep. The side edges of the slot have opposed longitudinal grooves such as is illustrated at 44.

FIGS. 4 and 5 illustrate the relative position of the hard insole with respect to the body of the boot. The boot has a 1½" horizontal stitched opening 46 in the seam of the boot between the upper portion of the boot and the bottom sole. Opening 46 provides access to slot 42 as well as permitting a visual inspection of the user's heel without removing the boot.

Hard insole 37 provides part of a splint bar assembly, the balance of the assembly being illustrated in FIG. 6. The assembly includes a leg bar or splint 48. The leg bar is also formed of a polypropylene material preferably 3" wide, 9" long and ¼" thick. The inside face of the leg bar has hook fabric fastener patches 49 for connecting the bar to the outside back surface of the boot.

Referring to FIG. 6, splint leg bar 48 has a pair of parallel lugs 50 and 52. The two lugs have four pairs of aligned openings 54, 56, 58 and 60. Hinge pin 62 is slideably received in aligned openings 54 with a slight friction fit so that it remains in the opening unless pushed out.

An angular hinge member 64 connects splint bar 48 to hard sole 37. Hinge member 64 has a longer leg 66, and a shorter leg 68 disposed at right angles to leg 66. Leg 66 has a 3¾" length permitting it to be inserted in heel opening 46 of the boot and into slot 42 of the hard sole. The opposite side edges of leg 66 have longitudinal tongues 70 and 72 which are slideably received in grooves 44 of the opposite side edges of slot 42, forming a tongue and groove connection between the hinge member and the hard sole. The tongues are frictionally retained in the grooves so that it requires some effort to pull the hinge member from the hard sole slot.

Short leg 68 of the hinge member has a 2" overall length including a tapered toe 74 and transverse openings 76 and 78.

When the short leg of the hinge member is inserted between the two lugs of the splint bar, opening 76 is aligned with opening 54 in the lugs. Hinge pin 62 is then inserted through the openings in the lugs and the hinge member so that the hinge member is pivotal with respect to the splint leg bar. The other opening 78 in the hinge member can then be aligned with either openings 56, 58 or 60 by swinging the hinge member.

When opening 78 is aligned with openings 60 in the lugs, a locking pin 80 is inserted in the aligned openings to connect the hinge member and the lugs in such a manner that the hard sole is disposed at a 90° angle with respect to the plane of the splint leg bar.

Referring to FIG. 4, if the hard sole is swung outwardly from the right angle position with respect to the plane of the leg bar, to align openings 78 with openings 56 in the lugs, locking pin 80 can then be inserted in these openings to lock the hard insole in a 30° position from the normal foot position so that the foot has an extension of 30°. This angle is illustrated by the numeral "X" in FIG. 4.

If the hard sole is pivoted to the left as illustrated in FIG. 4, from the 90° position, so tapered toe 74 is disposed beneath lug openings 58, the locking pin can be inserted to retain the hard sole in a +10° position, e.g. a condition of dorsi flexion.

In order to provide an incremental change in the angle of hard sole 37 with respect to the user's leg, a fabric sleeve 82 is illustrated in FIG. 9, mounted over the toe end of sole 37. The sleeve extends about two-thirds of the way down sole 37, and has a pocket 84 facing insole 36. Thus pocket 84 is on the same side of the hard sole as the user's foot.

Referring to FIG. 7, an inflatable, rectangular pleated bladder 86 is inserted in pocket 84 with its flat side 88 facing insole 36. Pocket 84 has a very large mouth with about a 2" opening for receiving bladder 86 so that side 88 of the bladder faces insole 36, just below the patient's toes. The bladder has a rectangular configuration, preferably about 3¾"×3½", and is formed of a rubber-like expansible air-tight material. A resilient outlet tube 90 is connected along the bladder's edge, in communication with the interior chamber of the bladder. Valve means 92 is connected to outlet tube 90 to control air flow from the bladder. A rubber, squeezable bulb 94 is connected by a flexible conduit 96 to the valve means. The bulb 94 is useful for inflating the bladder. Valve means 92 prevents air from exhausting from the bladder unless an outlet valve 98 is manipulated to exhaust air from the bladder.

When the bladder is fully deflated, it will reduce angle "X" by an amount "Y" that depends upon the thickness of the bladder. Angle "X" is the angle between the hard sole and a line drawn at a right angle to the user's leg. By inflating the bladder, angle "X" is reduced by an amount "Y" which is in proportion to the bladder degree of expansion. The treating nurse can increase "Y" in very small amounts by squeezing bulb 94, and reduce "Y" by releasing air from the bladder. The patient's foot can be adjusted easily and quickly in very small amounts to treat a foot that is subjected to contracture. Contracture is a state of contraction of the muscles. Thus, the splint provides means for accommodating a patient whose foot is in plantar flexion. The splint is not limited to fixed angles of flexion but can be easily adjusted in very small increments periodically to change the flexion of the patient's foot.

A smaller, manually inflatable bladder can also be used in other locations in connection with either the splint or the boot. For example, bladder 100 can be disposed beneath the user's ankle as illustrated in FIG. 5. Bladder 100 provides means for increasing the height of the user's ankle to accommodate the particular configuration of his heel to avoid contact with an abrasive surface. Bladder 100 is similar to bladder 86 except that it may be flatter. It is also inflated by a squeezable bulb and a control valve means (not shown).

Thus, it is to be understood that I have described an improved medical boot having a covering which is relatively non-abrasive to the user's skin by eliminating the conventional stitched seams around the edge of the covering and joining the seams by a hot-stamping process. Further, I have disclosed a means for very fine adjustments of the user's foot when supported in a splint by employing a pneumatically operated bladder. Other forms of bladders could be employed such as a hydraulic system.

Having described my invention, I claim:

1. A medical boot, comprising:

a substantially boot-shaped main body formed primarily of a substantially soft, flexible, compressible shape-retaining material having a hollow foot portion and a hollow leg portion;

splint means for supporting the limb of a patient, with the patient's foot disposed in the hollow foot portion of said boot-shaped main body;

said splint means comprising a relatively rigid sole (37) positioned in the hollow foot portion of the boot-shaped main body, a relatively rigid leg splint (48) positioned in the hollow leg portion of said boot-shaped body, hinge means for connecting the sole to the leg splint so that the sole can be adjusted angularly to have a multiple number of discrete angulations relative to the leg splint, and means for selectively locking the sole in discrete angular positions of adjustment with respect to said leg splint;

said rigid sole having one surface thereof facing the interior space defined by the hollow foot portion of said boot-shaped main body;

an insole positioned on said one surface of the rigid sole for contact with the bottom of the user's foot when the splint means is in use;

an inflatable member sandwiched between said one surface of the rigid sole and said insole; and manually-controllable means for incrementally adjusting the inflation pressure within said inflatable member, to produce minor adjustments in the position of said insole.

2. The medical boot, as defined in claim 1, wherein said inflatable member is located at an intermediate point along the length of said rigid sole, so that said inflatable member acts on an area of the insole located below the user's toes when the splint means is in use.

3. The medical boot, as defined in claim 1, and further comprising a pocket means (84) carried by said rigid sole in the space between the sole and the insole; said inflatable member being located within said pocket means.

4. The medical boot, as defined in claim 1, wherein said insole is formed of a soft, flexible, compressible shape-retaining material.

5. The medical boot, as defined in claim 1, wherein said boot-shaped main body has an access opening (46) located at the juncture between the hollow foot portion and the hollow leg portion; said access opening being of sufficient size to permit insertion of a portion of said hinge means into the hollow foot portion of said bootshaped main body.

6. The medical boot of claim 5, wherein said leg splint is located on the outer surface of said boot-shaped body, and including adhesive patch means (49) carried by said leg splint for releasably attaching said leg splint to said boot-shaped body.

7. The medical boot of claim 1, and further comprising a second hollow inflatable member positioned within said boot-shaped main body in registry with said leg splint;

said second inflatable member being located in near proximity to said hinge means to provide a cushioned support for the user's ankle when said splint means is in use.

8. The medical boot as defined in claim 1, wherein each of said hollow inflatable members comprises a bladder having two essentially flat walls connected at their peripheral edges, whereby said bladder has a pillow configuration in the inflated state.

9. A medical boot, comprising:

a substantially boot-shaped main body formed primarily of a substantially soft, flexible, compressible shape-retaining material having a hollow foot portion and a hollow leg portion;

splint means for supporting the limb of a patient, with the patient's foot disposed in the hollow foot portion of said boot-shaped main body;

said splint means comprising a relatively rigid sole (37) positioned in the hollow foot portion of the boot-shaped main body, a relatively rigid leg splint (48) positioned in the hollow leg portion of said boot-shaped body, hinge means for connecting the sole to the leg splint so that the sole can be adjusted angularly to have a multiple number of discrete angulations relative to the leg splint, and means for selectively locking the sole in said discrete angular positions of adjustment;

said rigid sole having one surface thereof facing the interior space defined by the hollow foot portion of said boot-shaped main body;

an insole positioned on said one surface of the rigid sole for contact with the bottom of the user's foot when the splint means is in use;

an inflatable member positioned within said boot-shaped body in registry with said leg splint; said inflatable member being located in near proximity to said hinge means to provide a cushioned support to the user's ankle when said splint means is in use; and manually-controllable means for incrementally adjusting the inflation pressure within said inflatable member, to produce minor adjustments in the position of said insole.

\* \* \* \* \*